United States Patent [19]

Kennedy, Jr. et al.

[11] 4,315,335
[45] Feb. 16, 1982

[54] DUAL SAFE HELMET

[76] Inventors: Alvin B. Kennedy, Jr., P.O. Box 282, Angleton, Tex. 77515; Steven W. Wright, 2917 Ocean Way, League City, Tex. 77573

[21] Appl. No.: 197,632

[22] Filed: Oct. 16, 1980

[51] Int. Cl.³ .......................... A61F 9/04; A62B 18/02
[52] U.S. Cl. .................................................. 2/424; 2/9; 128/201.23; 128/206.24
[58] Field of Search ...................... 2/424, 2.1 R, 2.1 A, 2/6, 10; 128/201.23, 201.24, 201.25, 201.27, 201.28, 201.29, 202.11, 206.24

[56] References Cited

U.S. PATENT DOCUMENTS

| | | | |
|---|---|---|---|
| 2,882,896 | 4/1959 | Seeler | 128/201.24 |
| 3,130,415 | 4/1964 | Colley | 2/6 |
| 3,362,403 | 1/1968 | Fleming et al. | 128/201.24 |
| 3,943,571 | 3/1976 | Boatman | 128/201.23 X |

Primary Examiner—Peter P. Nerbun
Attorney, Agent, or Firm—Guy E. Matthews

[57] ABSTRACT

Disclosed is a personnel protective apparatus which includes a helmet and a full face shield attachable to the helmet. The helmet includes a facial opening having a resilient edge roll thereabout. The face shield has a resilient seal bonded thereto which includes a face sealing portion adapted to form a seal about the face and a helmet sealing portion adapted to engage the edge roll and form a seal about the facial opening. The face sealing portion includes a first inwardly directed pressure energized seal which engages the face and a second outwardly directed pressure energized seal to engage the face. The helmet sealing portion includes a channel formed to encircle the face shield and cooperate with the edge roll of the helmet to urge the second shield into better sealing engagement with the face.

4 Claims, 6 Drawing Figures

DUAL SAFE HELMET

BACKGROUND OF THE INVENTION a. Field of the Invention

This invention relates generally to personnel protective apparatus, and more particularly to an improved helmet and face shield combination for use in contaminated atmopheres.

b. Description of the Prior Art

The National Institute for Occupational Safety and Health (NIOSH) defines a confined space as one which by design has limited openings for entry and exit, unfavorable natural ventilation which could contain or produce dangerous air contaminants, and which is not intended for continuous employee occupancy. Confined spaces include but are not limited to storage tanks, compartments of ships, process vessels, pits, silos, vats, degreasers, reaction vessels, boilers, ventilation and exhaust ducts, sewers, tunnels, underground utility vaults and pipelines. NIOSH also defines a confined space, class A, as a confined space, as previously defined, that presents a situation that is immediately dangerous to life or health. These include but are not limited to confined spaces having oxygen deficient, explosive or inflammable atmospheres, or concentrations of toxic substances.

Many devices have been used to lessen the effect of hazardous environments, including goggles around the eyes, filters around the nose, welding helmets in front of the face, and hard hats around the heat. Air lines have been attached to hoods drapped about the face to furnish a continuous flow of air within and from the hood, in the hope that no fumes or particles would enter the breathing zone of the person. Such devices may be helpful in mildly hazardous work areas; however, for use in confined spaces of the class A type, such devices are inadequate. Full face sealing air line and air pack respirators have been developed, but as yet, no system has been approved by NIOSH for use in confined spaces, class A.

It is therefore an object of the present invention to provide a personnel protective apparatus that will provide protection to personnel in confined spaces, class A.

SUMMARY OF THE INVENTION

Briefly stated, the foregoing and other objects and advantages of the present invention are accomplished by providing an apparatus including a helmet and a full face shield attachable to the helmet. The helmet includes a portion for covering the head and a facial opening having a resilient edge roll thereabout. The face shield is sized to cover the facial opening of the helmet, and includes a resilient seal bonded about the periphery thereof. The seal includes a face sealing portion adapted to form a seal about the face and a helmet sealing portion adapted to engage the edge roll of the helmet and form a seal therewith about the facial opening. The facial seal includes a first seal supported to contact and encircle the face of the person to form an inwardly directed pressure energized seal with the face. The face sealing portion also includes a second seal supported to encircle and contact the face outboard of the first seal to form an outwardly directed pressure energized seal with the face. The helmet sealing portion includes a channel formed in the resilient seal to encircle the shield outboard of the face sealing portion. The channel engages the edge roll to urge the second seal of the face sealing portion into sealing engagement with the face.

DESCRIPTION OF THE PREFERRED EMBODIMENT

Figure 1:
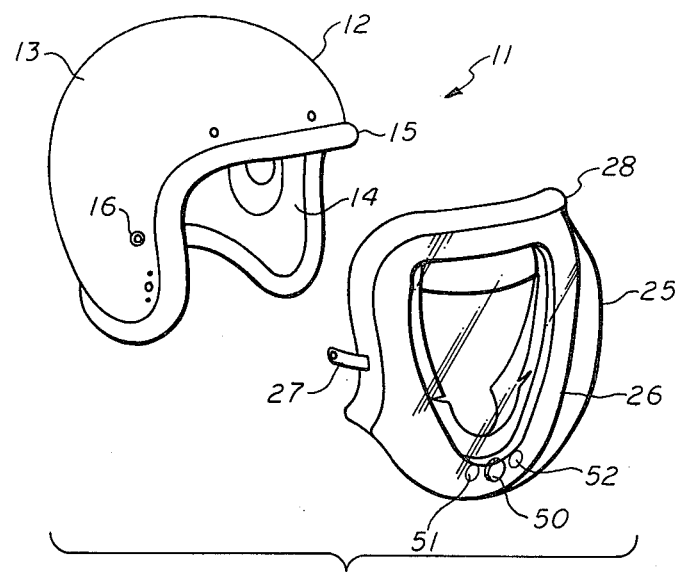
FIG. 1 is an isometric view of the helmet and face shield of the preferred embodiment of the present invention.
Figure 2:
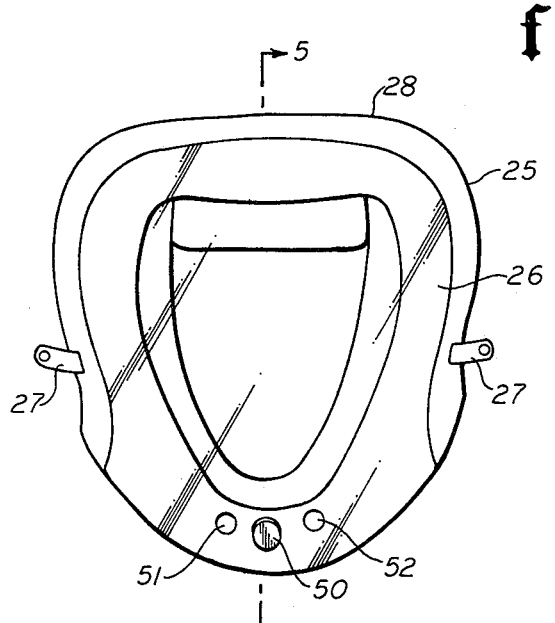
FIG. 2 is a front view of the face shield of the present invention.
Figure 3:
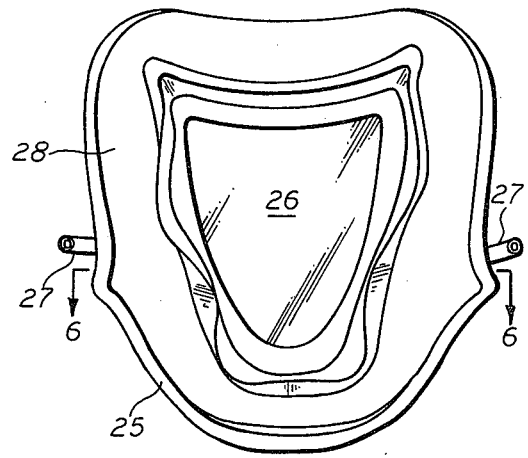
FIG. 3 is a back view of the face shield of the present invention.
Figure 4:
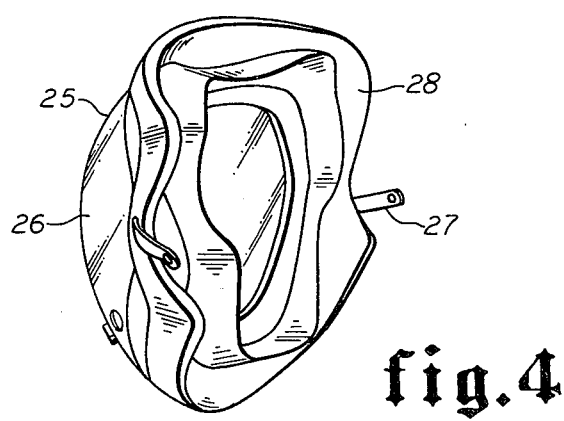
FIG. 4 is an isometric view of the face shield of the present invention.

Referring now to the drawings, and the first to FIG. 1, the apparatus of the present invention is designated generally by the numeral 11, and includes a helmet 12 and a full face shield 25. Helmet 12 is in the nature of aircraft crash helmet and includes an impact resistant head covering portion 13. Helmet 12 includes a frontal facial opening 14 which exposes the face of the wearer. Disposed about the edge of helmet 12 is a resilient edge roll 15. Helmet 12 includes a pair of face shield snap means, one of which is shown in FIG. 1 and designated by the numeral 16, for in the attachment of face shield 25 to helmet 12. Helmet 12 preferably includes suitable and conventional interior padding and webbing (not shown). Helmet 12 may also include a bone microphone and earphones (neither shown) for aiding in communication to and from the wearer.

Figure 5:
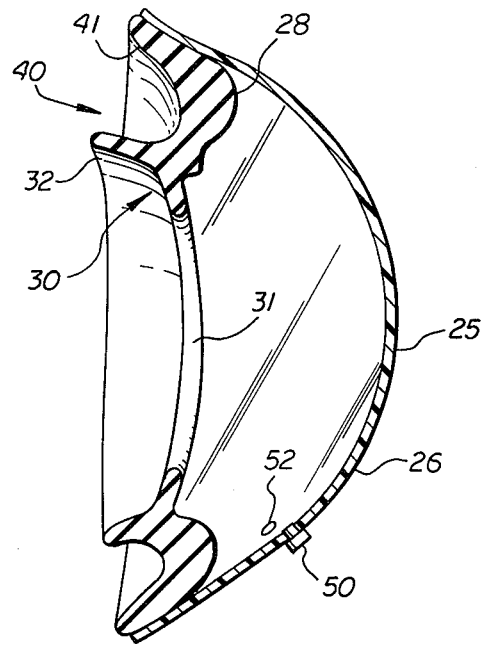
FIG. 5 is a sectional view taken along line 5—5 of FIG. 2 showing details of the face shield and resilient seal of the present invention.
Figure 6:
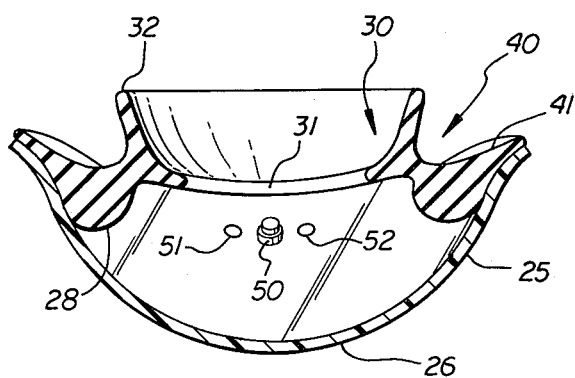
FIG. 6 is a sectional view taken along line 6—6 of FIG. 3 showing further details of the face shield and resilient seal of the present invention.

Face shield 25 includes a transparent portion 26 sized to cover fully the face of the wearer and facial opening 14 of helmet 12. Face shield 25 has attached thereto a pair of attachment straps 27, which are adapted to snap to attachment snaps 16 of helmet 12. Face shield 25 has bonded about the periphery thereof a resilient seal 28 referring particularly to FIGS. 5 and 6, resilient seal 28 includes a face sealing portion, designated generally by the numeral 30, which is adapted to form a seal with the face of the wearer, and a helmet sealing portion designated generally by the numeral 40, which is adapted to form a seal with the edge roll 15 of helmet 12. Resilient seal 28 is formed preferably of a nonporous material and is prestressed to conform sealingly with the face of the wearer. Face sealing portion 30 includes a first seal 31 supported to contact and encircle the face of the wearer to form an inwardly directed pressure energized seal with the face. Face seal 30 also includes a second seal 32 supported to contact and encircle the face of the wearer outboard of first seal 31 to form an outwardly directed pressure energized seal about the face.

Helmet sealing portion 40 includes a channel 41 that encircles the inner periphery of face shield 25 and is adapted to receive and seal therewith edge roll 15 of helmet 12. Edge roll 15 cooperates with channel 41 to urge second seal 32 into sealing engagement with the face of the wearer to form a more effective seal.

Face shield 25 is provided with a pressure demand exhalation valve 50 to allow exit of air from the interior of face shield 25 upon exhalation by the wearer. Valve 50 is set to maintain a positive pressure within face shield 25 which serves to urge first seal 31 of face seal 30 into engagment with the face of the wearer and to cause air to flow outwardly, rather than inwardly, in case of a seal failure.

Breathing air is supplied to the interior face shield 25 through a pair of pressure demand regulators 51 and 52. Pressure demand regulators 51 and 52 are are adapted to be supplied with air by independent sources of air such as a pair of flow lines leading to an air supply exterior of the work area or a self contained portable breathing pack. The pressure supplied to the interior face shield 25 is greater than the outside pressure in order to create a better seal between seal 31 and the face of the wearer.

From the foregoing, it will be seen that this invention is one well adapted to obtain all of the ends and objects hereinabove set forth, together with other advantages which are obvious and which are inherent to the apparatus. I will be understood that certain features and subcombinations are of utility and may be employed with reference to other features and subcombinations. This is contemplated by and is within the scope of the claims. As many possible embodiments may be made of the invention without departing from the scope hereof. It is to be understood that all matter herein set forth or shown in the accompanied drawings is to be interpreted as illustrative and not in a limiting sense.

What is claimed is:

1. A personnel protective apparatus, which comprises:

a helmet for covering the head of a person, said helmet including a facial opening having a resilient edge roll thereabout;

a full face shield attachable to said helmet to cover said facial opening, said face shield having a one piece nonporous resilient seal bonded thereto about the periphery thereof, said seal including a face sealing portion to form a seal about the face of the person and a helmet sealing portion adapted to engage said edge roll and form a seal about said facial opening;

said face sealing portion including a first seal supported to contact and encircle the face to form an inwardly directed pressure energized seal with the face, and a second seal supported to encircle and contact the face outboard of said first seal to form an outwardly directed pressure energized seal with the face;

and said helmet sealing portion including a channel formed in said resilient seal to encircle said full face shield outboard of said face sealing portion, said channel being configured to cooperate with said edge roll to urge said second seal of said face sealing portion into sealing engagement with the face.

2. The personnel protective apparatus as claimed in claim 1, including means for forming a positive pressure within said face shield when said face shield is sealed about the face.

3. The personnel protective apparatus as claimed in claim 2, wherein said positive pressure forming means includes dual air supply means mounted to said full face shield and a preset exhalation valve mounted to said full face shield.

4. A face mask for use with helmet leaving a facial opening with an edge roll thereabout, which comprises:

a transparent shield having a size sufficient to cover the face of a person wearing the helmet;

a one piece nonporous resilient seal bonded to and encircling the periphery of said shield, said seal including a channel extending completely about said seal and shield adapted to engage and seal with said edge roll, and a facial seal disposed inwardly of said channel and adapted to extend completely about and form a seal with the face of the person said facial seal including a first inwardly directed seal adapted to encircle and form a pressure energized seal with the face of the person, and a second outwardly directed seal adapted to encircle and form a pressure energized seal with the face of the person outwardly of said first inwardly directed seal.

* * * * *